United States Patent [19]

Melius et al.

[11] Patent Number: 5,651,778
[45] Date of Patent: Jul. 29, 1997

[54] FORMED INCONTINENCE ARTICLE AND METHOD OF MANUFACTURE

[75] Inventors: Mark Kevin Melius; Earle Harry Sherrod, both of Appleton; Lynn Kirkpatrick LeMahieu, Hortonville, all of Wis.

[73] Assignee: Kimberly-Clark Worldwide, Inc., Neenah, Wis.

[21] Appl. No.: 445,306

[22] Filed: May 19, 1995

Related U.S. Application Data

[62] Division of Ser. No. 165,153, Dec. 9, 1993.

[51] Int. Cl.$^6$ ................................................ A61F 13/15
[52] U.S. Cl. .................... 604/385.1; 604/367; 604/378; 604/387
[58] Field of Search ........................ 604/327, 329, 604/346–354, 358, 365, 366, 385.1–387, 378

[56] References Cited

U.S. PATENT DOCUMENTS

| D. 271,800 | 12/1983 | Brendling | D24/51 |
|---|---|---|---|
| D. 294,972 | 3/1988 | Nicklasson | D24/51 |
| 2,538,758 | 1/1951 | Bricmont | 128/287 |
| 3,030,958 | 4/1962 | Levin | 128/294 |
| 3,035,579 | 5/1962 | Benovic | 128/295 |
| 3,212,500 | 10/1965 | Bardy | 128/295 |
| 3,522,808 | 8/1970 | Worcester | 128/286 |
| 3,583,402 | 6/1971 | Cordell et al. | 128/295 |
| 3,805,790 | 4/1974 | Kaczmarzyk et al. | 128/290 R |
| 4,119,450 | 10/1978 | Bianco | 156/199 |
| 4,197,849 | 4/1980 | Bostick | 128/295 |
| 4,226,238 | 10/1980 | Bianco | 128/287 |
| 4,340,563 | 7/1982 | Appel et al. | 264/518 |
| 4,372,098 | 2/1983 | Mason | 53/412 |
| 4,405,297 | 9/1983 | Appel et al. | 425/72 S |
| 4,453,938 | 6/1984 | Brendling | 604/346 |
| 4,554,191 | 11/1985 | Korpman | 428/35 |

(List continued on next page.)

FOREIGN PATENT DOCUMENTS

| 0139484B1 | 5/1985 | European Pat. Off. . |
|---|---|---|
| 0140470B1 | 5/1985 | European Pat. Off. . |
| 0140471A1 | 5/1985 | European Pat. Off. . |
| 0140478 | 5/1985 | European Pat. Off. . |
| 0176853A1 | 4/1986 | European Pat. Off. . |
| 0186209 | 7/1986 | European Pat. Off. . |
| 0442223A1 | 8/1991 | European Pat. Off. . |
| 0483592A1 | 5/1992 | European Pat. Off. . |
| 0557677A1 | 9/1993 | European Pat. Off. . |
| 4096748 | 3/1992 | Japan . |
| 2059779 | 4/1981 | United Kingdom . |
| 2165755 | 4/1986 | United Kingdom . |
| 2182840 | 5/1987 | United Kingdom . |

(List continued on next page.)

*Primary Examiner*—John G. Weiss
*Assistant Examiner*—K. M. Reichle
*Attorney, Agent, or Firm*—Thomas M. Gage

[57] ABSTRACT

An incontinence article is manufactured by providing a formable, liquid impermeable moisture barrier material, an absorbent assembly, and a liquid permeable liner material. At least the moisture barrier, and desirably a composite structure including the moisture barrier, absorbent assembly and liner, are heated to the softening point of the moisture barrier. The composite structure is conformed such as by vacuum forming to the shape of a mold surface. Afterward, a shaped structure is recovered wherein the liner is bonded to the moisture barrier with the absorbent assembly sandwiched therebetween. The shaped structure, which may also include a retaining member and a cover, is adapted to fit the male anatomy and address urine-specific incontinence. The shaped structure includes a central portion and an ungathered peripheral wall outward of the central portion. The peripheral wall has a height above the central portion of at least about 5 millimeters transversely outward from a target zone and at least about 25 millimeters transversely outward from a transition zone. The shaped structure desirably has a Resulting Length of from about 10 to about 25 centimeters, a Body Conforming Angle of less than about 130 degrees, and a Skew Angle of at least about 15 degrees.

20 Claims, 9 Drawing Sheets

U.S. PATENT DOCUMENTS

| | | | |
|---|---|---|---|
| 4,559,051 | 12/1985 | Hanson | 604/385 R |
| 4,576,599 | 3/1986 | Lipner | 604/390 |
| 4,579,556 | 4/1986 | McFarland | 604/385 A |
| 4,668,230 | 5/1987 | Damico et al. | 604/385 A |
| 4,675,012 | 6/1987 | Rooyakkers | 604/349 |
| 4,677,810 | 7/1987 | Spano | 53/428 |
| 4,678,527 | 7/1987 | Ulman | 156/213 |
| 4,681,577 | 7/1987 | Stern et al. | 604/378 |
| 4,685,914 | 8/1987 | Holtman | 604/368 |
| 4,692,199 | 9/1987 | Kozlowski et al. | 156/245 |
| 4,701,177 | 10/1987 | Ellis et al. | 604/385 A |
| 4,710,188 | 12/1987 | Runeman | 604/385 R |
| 4,728,381 | 3/1988 | Jezuit et al. | 156/245 |
| 4,730,761 | 3/1988 | Spano | 225/2 |
| 4,731,063 | 3/1988 | Newkirk | 604/347 |
| 4,731,065 | 3/1988 | Yamada | 604/355 |
| 4,731,070 | 3/1988 | Koci | 604/385 R |
| 4,740,342 | 4/1988 | Menard et al. | 264/549 |
| 4,770,657 | 9/1988 | Ellis et al. | 604/385 A |
| 4,772,280 | 9/1988 | Rooyakkers | 604/349 |
| 4,772,282 | 9/1988 | Oakley | 604/385.1 |
| 4,778,372 | 10/1988 | Mutti et al. | 425/294 |
| 4,798,603 | 1/1989 | Meyer et al. | 604/378 |
| 4,798,638 | 1/1989 | Marbach | 156/69 |
| 4,814,123 | 3/1989 | Hautemont | 264/40.6 |
| 4,833,862 | 5/1989 | Bortolani et al. | 53/427 |
| 4,865,597 | 9/1989 | Mason, Jr. et al. | 604/385.1 |
| 4,886,509 | 12/1989 | Mattsson | 604/349 |
| 4,886,512 | 12/1989 | Damico et al. | 609/385.2 |
| 4,944,735 | 7/1990 | Mokry | 604/385.2 |
| 4,946,454 | 8/1990 | Schmidt | 604/385.1 |
| 4,950,262 | 8/1990 | Takagi | 604/385.1 |
| 5,013,309 | 5/1991 | Baigas, Jr. et al. | 604/368 |
| 5,030,229 | 7/1991 | Yang | 604/385.1 |
| 5,032,121 | 7/1991 | Mokry | 604/385.2 |
| 5,064,492 | 11/1991 | Friesch | 156/191 |
| 5,074,856 | 12/1991 | Coe et al. | 604/385.1 |
| 5,129,893 | 7/1992 | Thoren | 604/385.2 |

FOREIGN PATENT DOCUMENTS

| | | |
|---|---|---|
| WO85/03428 | 8/1985 | WIPO . |
| WO86/05387 | 9/1986 | WIPO . |
| WO86/06621 | 11/1986 | WIPO . |
| WO86/06620 | 11/1986 | WIPO . |
| WO87/01914 | 4/1987 | WIPO . |
| 8707136 | 12/1987 | WIPO . |
| WO91/07155 | 5/1991 | WIPO . |
| WO91/16870 | 11/1991 | WIPO . |
| WO92/01431 | 2/1992 | WIPO . |
| WO92/15269 | 9/1992 | WIPO . |
| WO93/16666 | 9/1993 | WIPO . |

FORMED INCONTINENCE ARTICLE AND METHOD OF MANUFACTURE

This is a divisional application of copending application U.S. Ser. No. 08/165,153, filed on Dec. 9, 1993.

BACKGROUND OF THE INVENTION

The present invention relates to articles for absorbing body fluids, and particularly those body fluids discharged in the crotch area. It also relates to methods of making such absorbent articles.

Disposable absorbent products have been known for some time. Typical of such products are disposable diapers, feminine sanitary napkins, incontinence pads, and the like. Such products contain an absorbent medium which is usually placed between a liquid impermeable backing material and a liquid permeable bodyside liner. Despite the substantial amount of work that has been done in developing such products, there remains a need for a functional, and yet desirably concealable, product for adult urinary incontinence, especially for male incontinence.

Urine incontinence is an increasingly recognized problem, especially among older persons. Urine incontinence may range from involuntarily leaking small amounts of urine, such as a few drops, to totally voiding the bladder.

While the incidence of urine incontinence is greater for females than males, many males as well suffer at one time or another from urine incontinence. To date, however, incontinence products have not been adequately designed for males to yield comfortable, discreet, urine-specific incontinence protection, covering the range from drops to total voiding.

Therefore, what is lacking and needed in the art is an absorbent article capable of efficient manufacture that not only addresses urine-specific incontinence over a wide range of penis sizes and insult volumes, but also fits the male anatomy comfortably and discretely.

SUMMARY OF THE INVENTION

In response to the discussed deficiencies in the prior art, a new disposable absorbent article has been developed. Articles of the present invention comfortably contain the male genitalia, reduce leakage and promote dryness. In one embodiment, an absorbent article of the present invention has longitudinal and transverse axes and generally includes a shaped structure with opposite forward and rearward longitudinally-spaced edges. The shaped structure includes a central portion with an ungathered peripheral wall outward of the central portion. The central portion includes a target zone longitudinally separated from a secondary zone by a transition zone, where the target zone is located toward the forward edge and the secondary zone is located toward the rearward edge. The peripheral wall that is transversely outward from the target zone has a height above the target zone of at least about 5 millimeters, while the peripheral wall that is transversely outward from the transition zone has a height above the transition zone of at least about 25 millimeters. The shaped structure has a Resulting Length of from about 10 to about 25 centimeters, a Body Conforming Angle of less than about 130 degrees, and a Skew Angle of at least about 15 degrees. The shaped structure includes a liquid storage layer with a periphery, a moisture barrier formed of formable, liquid impermeable material, and a liner formed of liquid permeable material. The storage layer is located in the central portion, and the peripheral wall is located outward of the storage layer periphery. The moisture barrier defines a basin having a length, width and volume. The liquid storage layer is positioned in the basin and sandwiched between the liner and the moisture barrier, which are bonded together.

This aspect of the invention yields a relatively short article targeted for urine incontinence. In use, the article is positioned forward of the anus of the wearer so that the wearer generally does not sit on the article. Thus, the absorbent assembly is less subject to bunching and twisting and can be economically manufactured.

In another embodiment, the shaped structure further includes a retaining member bonded to the moisture barrier. The retaining member defines a compartment between the liner and the retaining member. The compartment has an opening located within about 20 centimeters of the rearward edge, and a volume of at least about 25 cubic centimeters. The shaped structure also includes a cover formed of a liquid impermeable material that is bonded to the moisture barrier near the rearward edge. The cover has a surface area of from about 13 to about 194 square centimeters.

This aspect of the invention provides an especially dry environment for the wearer. The retaining member holds the penis of the wearer in its proper position, while the cover protects against leakage past the rearward end of the abbreviated article. The penis is held in the compartment with the scrotum resting on the cover.

As set forth more fully below, absorbent articles of the present invention define shaped structures that are tailored to fit the male anatomy. The shaped structures fit closely around the genital region of the wearer and snugly cup the genitals. In particular embodiments of the invention, the shaped structure has a Body Conforming Angle of less than about 120 degrees, and particularly about 115 degrees. The shaped structures cup the scrotum without extending rearwardly to the anus. Thus, in particular embodiments, the shaped structures desirably have a Skew Angle of at least about 20 degrees, more desirably at least about 40 degrees, a Resulting Length of about 20 centimeters, and a Resulting Width that narrows toward the rearward edge.

Another aspect of the invention pertains to a method of making an absorbent garment. This method includes: providing a first continuous web of formable, liquid impermeable material; providing an absorbent assembly comprising a liquid Storage layer; providing a second continuous web of liquid permeable material; heating at least the first continuous web to its softening point; assembling a composite structure comprising the first and second continuous webs and the absorbent assembly sandwiched therebetween; positioning the composite structure over a mold surface with the first continuous web facing away from the mold surface; conforming the composite structure to the mold surface by the application of pressure; and recovering from the composite structure a shaped structure having a liquid permeable liner bonded to a liquid impermeable moisture barrier with the absorbent assembly sandwiched therebetween. In one embodiment, the shaped structure has a Body Conforming Angle of less than about 130 degrees. In other embodiments, the method also includes: bonding a retaining member to the shaped structure to define a compartment having an opening and a volume of from about 25 to about 245 cubic centimeters; and bonding a cover formed of a liquid impermeable material having a surface area of from about 13 to about 194 square centimeters to the shaped structure.

As can be seen from the foregoing, an absorbent article of the present invention provides urine-only incontinent individuals a dry environment for the penis and scrotum, in a shaped structure that is comfortable and discreet to wear. Articles of the invention can be efficiently manufactured because the primary components are shaped and bonded together in a single step.

Numerous other benefits and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

BRIEF DESCRIPTION OF THE DRAWINGS

FIG. 9A illustrates a desired shape of the disposable absorbent articles shown in FIG. 1, while

DEFINITIONS

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposable" includes being disposed of after use, and not intended to be washed and reused.

(c) "disposed", "disposed on", "disposed with", "disposed at", "disposed near", and variations thereof are intended to mean that one element can be integral with another element, or that one element can be a separate structure joined to or connected to or placed with or placed near another element.

(d) "elastic" and "elasticity" include that property of a material by virtue of which it tends to recover its original size and shape after removal of a force causing the deformation.

(e) "formed" and "formable" describe the condition or property of a material to be conformable to a three-dimensional shape and thereafter generally retain the three-dimensional shape, for example, through the application of heat and pressure to the material in manufacturing processes such as thermoforming, vacuum forming, injection molding, mechanical forming, or the like.

(f) "front" and "back" are used to designate relationships relative to the garment itself, rather than to suggest any position the garment assumes when it is positioned on a wearer.

(g) "liquid communication" means that liquid is able to pass between the specified layers.

(h) "member" when used in the singular can have the dual meaning of a single element or a plurality of elements.

These definitions are not intended to be limiting, and these terms may be defined with additional language in the remaining portion of the specification.

DETAILED DESCRIPTION OF THE PREFERRED EMBODIMENTS

Figure 1:
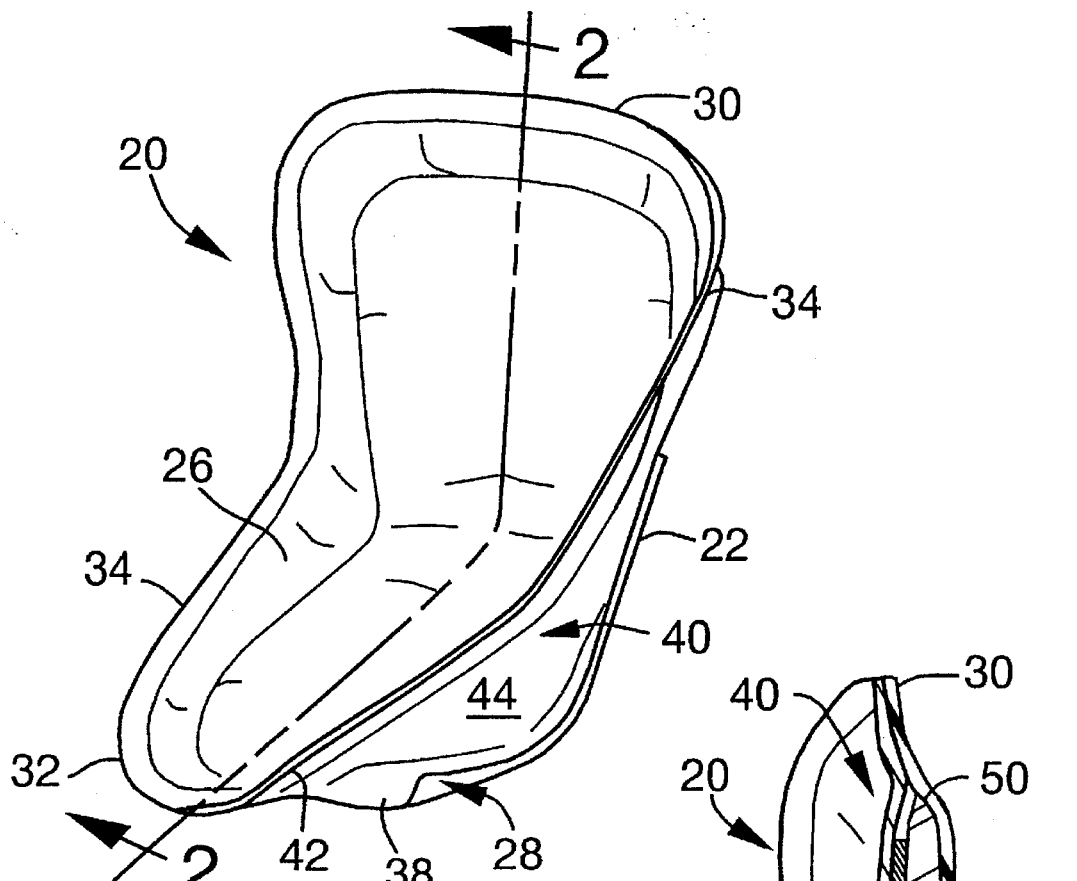
FIG. 1 is a perspective view of a disposable absorbent article according to the present invention.
Figure 2:
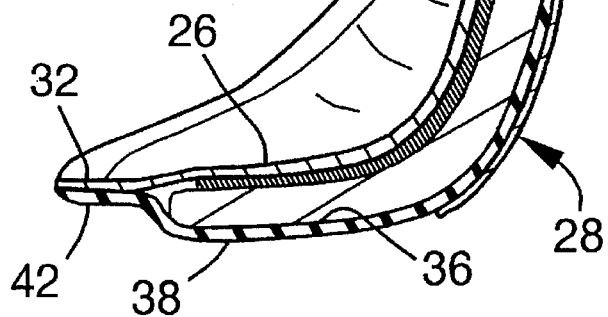
FIG. 2 is a longitudinal section view taken generally from the plane of the line 2—2 in FIG. 1.

Absorbent articles of the present invention are concerned primarily with providing absorbent protection for males suffering from urinary incontinence. Referring to FIGS. 1 and 2, a disposable absorbent article 20 according to the present invention includes a moisture barrier 22, an absorbent assembly 24, a liner 26 and attachment means 28.

The illustrated moisture barrier 22 is formed from a flexible, formable material that is substantially liquid impermeable. Exemplary materials suitable for use in forming the moisture barrier 22 are various thermoplastic or thermosetting polymeric resins such as polyethylene, polypropylene, polyurethane, polyesters, or the like. In one particular embodiment of the present invention, the moisture barrier 22 is formed from a thin layer of closed-cell, cross-linked polyethylene foam, which may contain a vinyl-acetate comonomer, commercially available from Voltek Inc. of Lawrence, Mass. USA, under the trade designation Volara. The foam material prior to forming desirably has a density of about 24 to about 96 kg/m$^3$ and a thickness of about 1.6 to about 9.5 millimeters. Other thermoplastic or thermosetting polymeric foams and materials, such as films, are suitable for use in the present invention.

The moisture barrier 22 desirably possesses sufficient structural rigidity to form a stand-alone, three-dimensional shell. In such a case, the moisture barrier suitably has a formed thickness of from about 1.1 to about 2.0 millimeters, and desirably from about 1.6 to about 1.8 millimeters. In any event, the moisture barrier 22 is generally sufficiently flexible to readily conform to pressures exerted on it during use by a wearer. The moisture barrier 22 can be formed from a variety of manufacturing processes such as thermoforming, vacuum forming, injection molding, mechanical forming, or the like.

The moisture barrier 22 has a forward edge 30, a rearward edge 32 longitudinally spaced from the forward edge, and a pair of side edges 34 extending between the forward and rearward edges. The periphery of the moisture barrier 22 may comprise smooth curves as shown in FIG. 1, rendering the distinction between the edges imprecise near the corners. The moisture barrier 22 also has opposite major surfaces designated inner surface 36 and outer surface 38. As formed, the moisture barrier 22 defines a basin 40 and a rim 42. The basin 40 includes sidewalls 44 and has a length, width, and volume. The rim 42 is desirably continuous around the periphery of the basin 40 and has a generally uniform width.

To obtain the desired finished shape of the absorbent article 20, the moisture barrier 22 desirably has a, length of from about 12 to about 38 centimeters, particularly about 33 centimeters. The length of the moisture barrier 22 is measured along the outer surface 38 between the forward and rearward edges 30 and 32. Additionally, the moisture barrier 22 desirably has a width in the range of from about 7 to about 20 centimeters, particularly about 15 centimeters. The width of the moisture barrier 22 is measured along the outer surface 38 between the side edges 34. The width of the moisture barrier 22 material desirably narrows toward the rearward edge 32.

The absorbent assembly 24 (FIG. 2) is positioned in the basin 40 against the inner surface 36 and is desirably formed to be sufficiently flexible to readily conform to the contour of the inner surface. The absorbent assembly 24 is positioned against, particularly directly against, the inner surface 36 and may be attached thereto using adhesives or other suitable means.

The absorbent assembly 24 is sized to reside within the basin 40. Furthermore, because the basin 40 may function to both contain urine and house portions of the male genitalia, the absorbent assembly 24 desirably resides toward the bottom of the basin. In particular, the absorbent assembly 24 desirably fills less than about 60 percent, more desirably less than about 20 percent, of the volume of the basin. By way of example, the absorbent assembly 24 may be irregularly shaped with a length in the range of about 8 to about 36 centimeters and a width in the range of about 1 to about 19 centimeters, desirably narrower toward the rearward edge 32. As a result, the sidewalls 44 extend above the absorbent assembly 24 and establish space within the basin 40 for male genitalia.

The absorbent assembly 24 comprises a liquid storage layer 46 formed of a material adapted to absorb and retain urine, and optionally, an acquisition layer 48 (FIG. 2). The absorbent assembly 24 is generally configured according to the amount of liquid intended to be absorbed, and the absorbent rate and capacity of the assembly components. In particular, the, storage layer 46 suitably has a capacity of urine of from about 50 to about 300 grams, particularly about 150 grams. The urine capacity of the storage layer 46 is its saturated retention capacity, which is a measure of the total absorbent capacity of an absorbent garment, material or structure.

Saturated retention capacity of the storage layer 46 may be determined as follows. The material to be tested, having a moisture content of less than about 7 weight percent, is weighed and submerged in an excess quantity of room temperature (about 23 degrees Celsius) synthetic urine. The material to be tested is allowed to remain submerged for 20 minutes. After 20 minutes, the material is removed from the urine and placed on a "Teflon" coated fiberglass screen having 0.25 inch openings (commercially available from Taconic Plastics Inc., Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The material is weighed. The amount of fluid retained by the material being tested is determined by subtracting the dry weight of the material from the wet weight of the material (after application of the vacuum) and is reported as the saturated retention capacity in grams of fluid retained. For relative comparisons, this value can be divided by the weight of the material to give the saturated retention capacity in grams of fluid retained per gram of tested material.

The synthetic urine composition referenced herein comprises 0.31 grams monobasic calcium phosphate monohydrate ($CaH_4(PO_4)_2H_2O$), 0.68 grams monobasic potassium phosphate ($KH_2PO_4$), 0.48 grams magnesium sulphate heptahydrate ($MgSO_4\ 7H_2O$), 1.33 grams potassium sulphate ($K_2SO_4$), 1.24 grams tri basic sodium phosphate dodecahydrate ($Na_3PO_4\ 12H_2O$), 4.4 grams sodium chloride (NaCl)., 3.16 grams potassium chloride (KCl). 8.56 grams of urea ($CO(NH_2)_2$), 0.1 grams Pluronic 10R8 surfactant (a nonionic surfactant commercially available from BASF-Wyandotte Corporation) and 1 gram methyl pareben and 1 gram Germall 115 preservative (commercially available from Santell Chemical Company, Chicago, Ill.) per liter using distilled water as the solvent. The components are added to 900 milliliters of distilled water in the order given and each dissolved before the next component is added. The solution is finally diluted to one liter.

If material, such as high-absorbency material or fiber is drawn through the fiberglass screen while on the vacuum box, a screen having smaller openings should be used. Alternatively, a piece of tea bag material can be placed between the material and the screen and the final value adjusted for the fluid retained by the tea bag material. Suitable tea bag material, is a heat sealable tea bag material grade 542, commercially available from Kimberly-Clark Corporation. The amount of fluid absorbed by the tea bag material is determined by performing the saturated retention capacity test on an empty tea bag. Testing high-absorbency materials or fibers alone can be accomplished using a sealed pouch of tea bag material.

The liquid storage layer 46 is desirably smaller in length and width than the moisture barrier 22 and defines a periphery 50. The storage layer 46 may have a thickness of from about 0.2 to about 1 centimeter and a density of from about 0.1 to about 0.3 grams per cubic centimeter. One suitable storage layer 46 comprises an airlaid batt of wood pulp fluff and high absorbency materials, as hereinafter described, with a thickness of about 0.5 centimeter and a density of about 0.18 grams per cubic centimeter.

The acquisition layer 48 is superposed on top of and in liquid communication with the storage layer 46. Dots or lines of adhesives, ultrasonic bonds or other suitable means may be employed to bond the acquisition layer 48 to the storage layer 46. The acquisition layer 48 may be generally the same size and shape as the storage layer 46.

The acquisition layer 48 can be or can contain any suitable material for managing, transporting, accommodating, permitting, or directing rapid and/or sudden flow of urine therethrough and into contact with the storage layer 46. The acquisition layer 48 desirably functions to draw liquid from the liner 26 and then permit desorption by the storage layer 46. One suitable material for the acquisition layer 48 is a latex bonded polyester, which is available from Sackner Products of Grand Rapids, Mich. under the trade designation SH-66. Other suitable materials are disclosed in U.S. Pat.

No. 4,798,603 issued Jan. 17, 1989, to Meyer et al., which is incorporated herein by reference.

The liner 26, which is formed of a substantially liquid permeable material, is positioned to sandwich the absorbent assembly 24 between the liner and the moisture barrier 22. Desirably, the liner 26 is thermally or physically bonded to the moisture barrier 22 outward of the periphery 50 of the storage layer 46. For example, the liner 26 may be physically bonded to the rim 42 and portions of the sidewalls 44, as shown in FIGS. 1 and 2. Alternately, the moisture barrier 22 and liner 26 may be bonded together using adhesives, ultrasonic bonds or other suitable means. The liner 26 may also be bonded directly to the absorbent assembly 24 using thermal bonds, adhesives, ultrasonic bonds or other suitable means. In an alternate embodiment, the liner 26 is positioned directly over the storage layer 46 and the acquisition layer 48 is bonded to the surface of the liner that is remote from the storage layer 46 (not shown).

Figure 3:
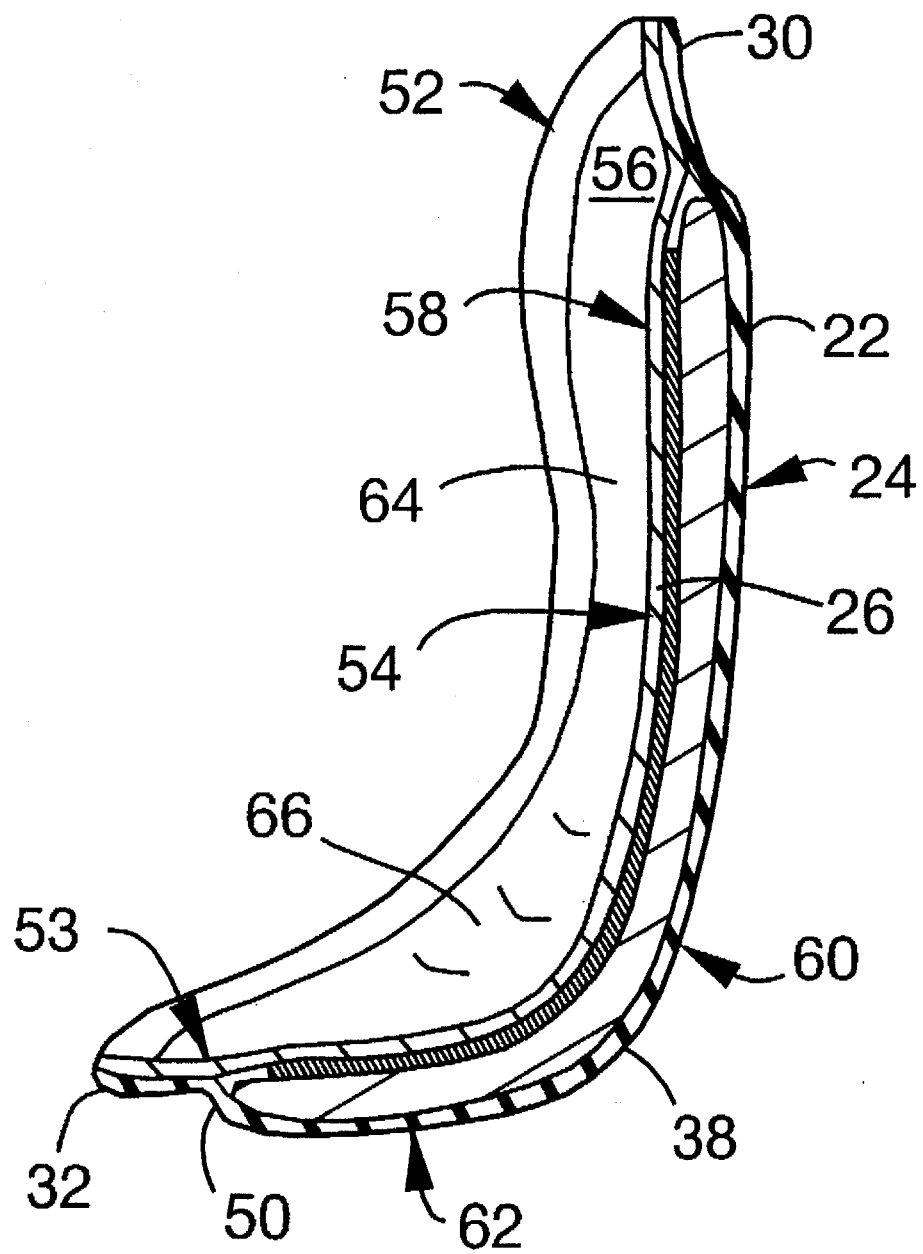
FIG. 3 is a longitudinal section view similar to FIG. 2 showing a shaped structure without a garment attachment means.
Figure 4:
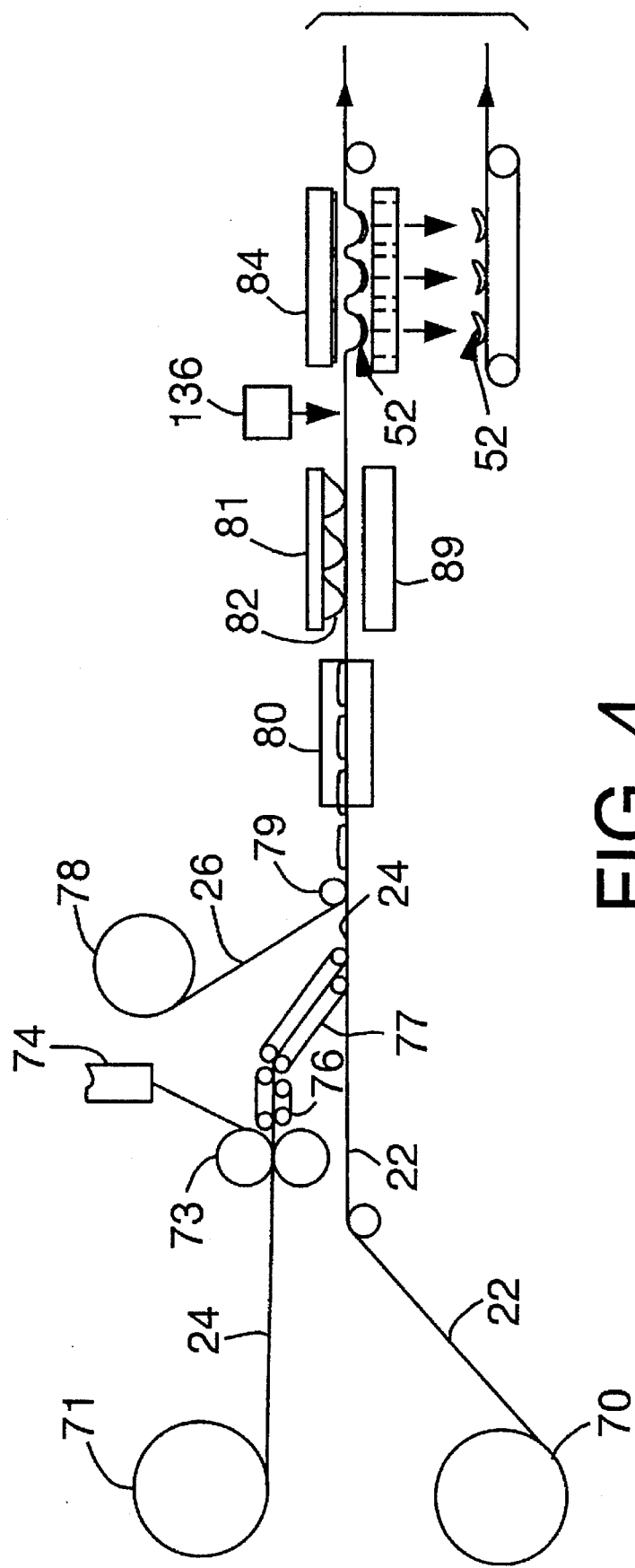
FIG. 4 is a schematic representation of a manufacturing process for making the absorbent article shown in FIG. 1.

The moisture barrier 22, absorbent assembly 24, and liner 26 define a shaped structure, which is designated reference numeral 52 in FIGS. 3 and 4. The shaped structure 52 is particularly well suited to accommodate the male genitalia and handle urine-specific incontinence. The shaped structure 52 includes a body facing surface 53, which corresponds to the surface of the liner 26 that is remote from the absorbent assembly 24, and an opposite garment facing surface, which corresponds to the outer surface 38 of the moisture barrier 22. The shaped structure 52 also includes a central portion 54 with a peripheral wall 56 outward of the central portion. The term "outward" is intended to mean transversely and/or longitudinally away from the longitudinal and transverse center of the absorbent article 20. The terms "longitudinal" and "transverse" have their customary meaning, as indicated by longitudinal section line 2—2 in FIG. 1 through the absorbent article 20.

The central portion 54 constitutes those portions of the shaped structure 52 where the storage layer 46 is located. Correspondingly, the peripheral wall 56 constitutes those portions of the shaped structure 52 that are outward of the periphery 50 of the storage layer 46. In the illustrated embodiment, the peripheral wall 56 generally corresponds to the sidewalls 44 of the moisture barrier 22.

The central portion 54 includes a target zone 58, a transition zone 60, and a secondary zone 62. The target and secondary zones 58 and 62 are longitudinally separated by the transition zone 60. As illustrated, the target zone 58 is located toward the forward edge 30 of the moisture barrier 22 and is desirably wider than the secondary zone 62. The width being considered is that generally perpendicular to the longitudinal axis of the absorbent article 20. The secondary zone 62 is located toward the rearward edge 32, while the transition zone 60 is desirably located in the highly curved and deep portion of the shaped structure 52.

For the basin 40 to contain urine and house the male genitalia, the peripheral wall 56 desirably extends above the central portion 54 about the entire periphery 50 of the storage layer 46. Alternately, the peripheral. Wall 56 can extend above the central portion 54 only along the forward edge 30 and each side edge 34 (FIG. 3). More precisely, the peripheral wall 56, at locations transversely outward from the target zone 58, such as at point 64 in FIG. 3, desirably has a height above all portions of the target zone of at least about 5 millimeters, and particularly from about 12 to about 20 millimeters. Also, at locations transversely outward from the transition zone 60, such as at point 66 in FIG. 3, the peripheral wall 56 desirably has a height above all portions of the transition zone of at least about 5 millimeters, more desirably a height greater than that transversely outward from the target zone 58 such as at least about 25 millimeters, and particularly from about 35 to about 51 millimeters. The height of the peripheral wall 56 above a particular portion of the central portion 54 is the maximum distance between a first plane tangent,to the, body facing surface 53 at that portion and a second plane parallel to the first plane and intersecting the, peripheral wall, either longitudinally or transversely outward from the particular portion depending upon the height being measured.

To promote air circulation, the peripheral wall 56 is desirably slightly contoured along the forward edge 30. To accomplish this, the height of the peripheral wall 56 above the target zone 58 transversely outward from the target zone, for example near the corners between the forward edge 30 and the side edges 34, is desirably greater than the height of the peripheral wall above the target zone longitudinally outward from the target zone.

For use as a male incontinence product, the transition zone 60 desirably corresponds to the deepest portion of the shaped structure 52. Furthermore, the transition zone 60 is desirably skewed toward the rearward edge 32 of the shaped structure 52. For example, the transition zone 60 is desirably located about midway between the rearward edge 32 and the longitudinal center of the article 20.

The absorbent article 20 may be constructed by separately forming each element and bonding the elements together with adhesives, thermal bonds, ultrasonic bonds or other suitable means. More desirably, however, the absorbent article 20 can be manufactured according to the process schematically illustrated in FIG. 4.

A continuous web of formable moisture barrier material 22 is provided from supply roll 70 and fed to a processing line. Absorbent material 24, which may represent a composite web comprising a storage layer 46 and an acquisition layer 48, is provided from supply roll 71 and fed to a cutting station 73. Individual absorbent assemblies 24 are cut from the web of absorbent material, for instance with a rotary cutter. Waste material from the cutting operation may be directed to receptacle 74. Conveyors 76 and 77 advance the absorbent assemblies 24 and position them on the continuous web of moisture barrier material 22. The absorbent assemblies 24 can be provided in a single line or alternately in multiple lines (not shown).

Figure 5:
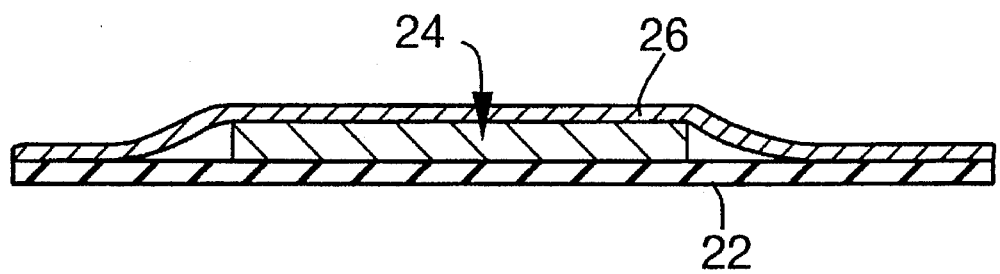
FIG. 5 is a view in vertical section of components of the absorbent article shown in FIG. 1 during an intermediate stage of the manufacturing process illustrated in FIG. 4.

A continuous web of liner material 26 is provided from supply roll 78. The liner material 26 is routed under roll 79 to form a loose composite structure of the moisture barrier and liner materials with the absorbent assemblies 24 sandwiched therebetween, as shown in FIG. 5.

The composite structure is routed into heating oven 80, where the structure is maintained until the temperature of the moisture barrier material 22 is elevated to its softening point. Alternately, the moisture barrier material 22 alone could be heated prior to being united with the absorbent assemblies 24 and the liner material 26 (not shown). In one embodiment, the moisture barrier material 22 is a crosslinked polyethylene foam having a density of about 44 $kg/m^3$ and a thickness of about 2 millimeters, and the composite structure is heated in oven 80 to a temperature of about 115 to 157 degrees Celsius, particularly about 149 degrees Celsius, for a period of about 5 to about 18 seconds, particularly about 8 seconds. Heating temperatures and times will, of course, depend upon the materials selected for the article 20.

Figure 6:
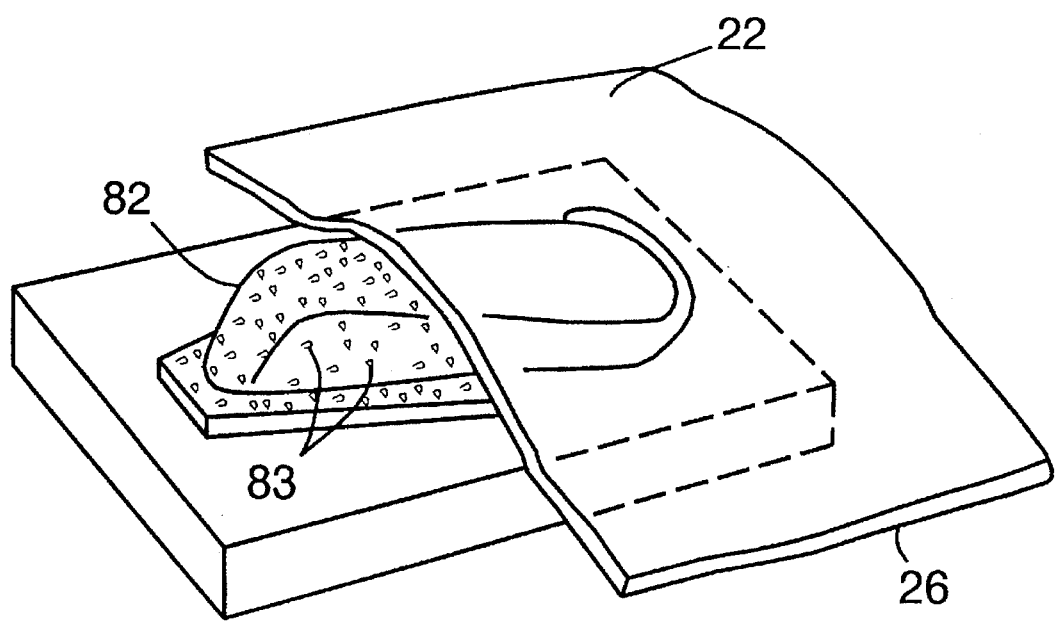
FIG. 6 is a perspective view illustrating the components of FIG. 5 positioned above forming equipment used in the manufacturing process shown in FIG. 4, the components shown partially broken away for purposes of illustration.
Figure 7:
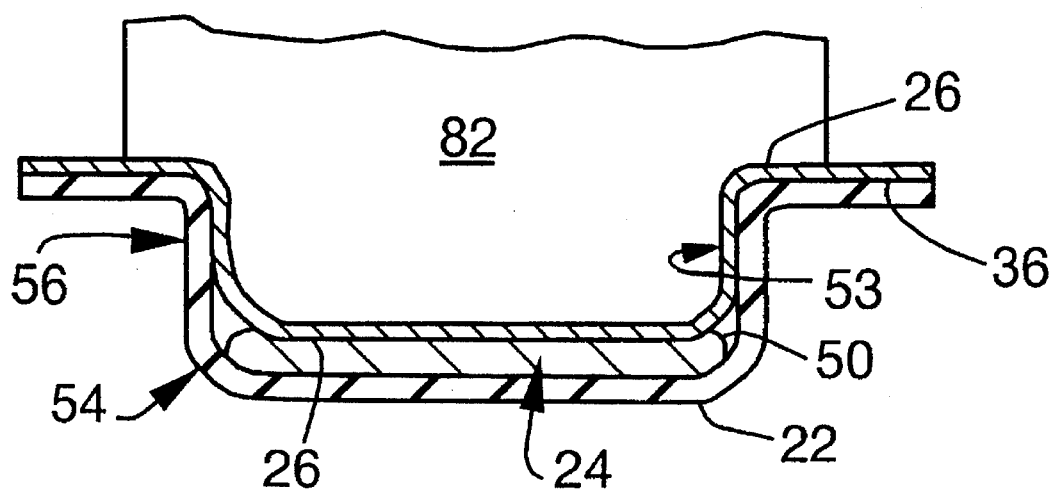
FIG. 7 is a View in vertical section of the components and forming equipment of FIG. 6 at a later stage of the manufacturing process illustrated in FIG. 4.

The heated composite structure is next advanced to vacuum thermoforming station 81 where the structure is formed on downwardly projecting male mold surfaces 82. With additional reference to FIGS. 6 and 7, the composite structure is positioned such that the liner material 26 is facing the mold surface 82 while the moisture barrier material 22 is facing away from the mold surface. Further, the absorbent assembly 24 is aligned with the contoured center portion of the mold surface 82. A frame 89 or other suitable means may be employed to form a seal between the composite structure and the periphery of the vacuum station 81. This seal allows the composite structure to be vacuum drawn onto the mold surface 82. In particular, the moisture barrier material 22 is gas impermeable and is thus drawn onto the mold surface 82, trapping the liner 26 and absorbent assembly 24 therebetween. Alternately, the composite structure may be thermoformed using plug assist, both male and female molds, drape forming or other suitable techniques (not shown).

As vacuum is applied through vacuum channels 83 (FIG. 6), the softened moisture barrier material 22 has a tacky inner surface 36 which bonds to adjacent portions of the liner 26, and desirably also to the absorbent assembly 24. At least the fibers of the liner 26 tend to become embedded into the soft inner moisture barrier surface 36 and physically bonded thereto. Thus, the thermoforming step results in a plurality of shaped structures 52 being formed in the composite structure, while also bonding the structure components together.

Notably, the moisture barrier 22 and liner 26 are directly bonded together over the entire peripheral wall 56. This bonding assists in holding the shaped structure 52 in the desired shape without the use of intervening adhesives. This bonding also creates sufficient space above the body facing surface 53 and within the peripheral wall 56 to house the genitals of a male wearer. Further, the absorbent assembly 24 will be trapped in position even though there may be little direct bonding between the absorbent assembly and the moisture barrier 22. The absorbent assembly 24 will be held in place against sagging, and the single forming and bonding step will minimize wrinkles and folds between the liner and moisture barrier.

After the thermoforming step, the composite structure is advanced to a trimming station 84. The trimming station 84 may comprise a stamping unit, or alternately a rotary cutter (not shown). The individual shaped structures 52 are recovered from the continuous composite structure, with waste material being removed. Attachment means 28 (FIGS. 1 and 2), for example garment attachment adhesive and a strip of release paper used to secure the shaped structure to underclothing of a wearer, may be applied to the shaped structures 52 to complete assembly of the absorbent article 20.

Figure 8:
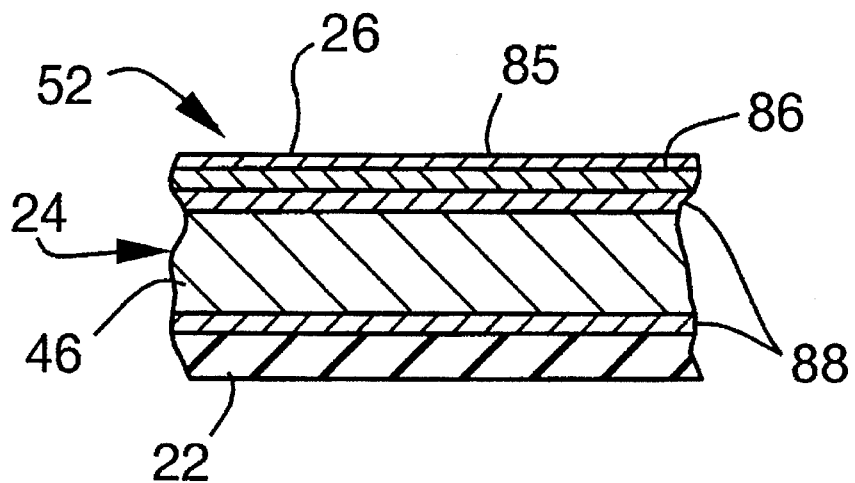
FIG. 8 is an enlarged view in vertical section illustrating alternate components for use in manufacturing the disposable absorbent article of FIG. 1.

An alternate shaped structure 52 including modified materials is partially shown in FIG. 8, where components similar to those previously described have been given the same reference numeral. The modified materials allow the absorbent assembly 24 and liner 26 to thermally bond with the moisture barrier 22. The term "thermally bond" is used herein to refer to two materials being bonded together by the mutual softening of each material, in contrast to bonding where only one of the materials is softened and the other material embedded in the softened material.

The liner 26 illustrated in FIG. 8 is generally formed as a two layer composite, with a first layer 85 of a spunbond polyolefin, desirably containing polypropylene, and a second layer 86 of carded fibers attached to the first layer in a known manner. The liner 26 may comprise about 75 percent polypropylene fiber and about 25 percent polyester fiber. Alternately, the liner composition may include about 10 to 100 percent, particularly about 10 to 70 percent, and more particularly 10 to 40 percent, of a fiber capable of being thermally bonded to the moisture barrier 22 under heating and bonding conditions suitable for the moisture barrier. Thus, a portion of the fibers in the liner 26 are desirably selected in view of the moisture barrier material 22. For example, where the moisture barrier 22 comprises a polyethylene foam, a portion of the fibers in liner 26 also comprise a polyethylene composition.

The absorbent assembly 24 illustrated in FIG. 8 includes a liquid storage layer 46 sandwiched between carrier sheets 88, for example a 24 gram per square meter tissue formed from wood pulp. In one embodiment, the storage layer 46 is fabricated in a melt blowing process wherein polypropylene fibers are melt blown onto a carrier sheet 88. In the melt blowing process, additional fibers such as wood pulp fluff and/or high-absorbency materials are mixed with the polypropylene fibers such that the composite of the additional fibers and the polypropylene fibers is impinged upon the carrier sheet 88.

To promote thermal bonding of the absorbent assembly 24 and liner 26 to the moisture barrier 22, the second layer 86 of the liner and the carrier sheet 88 adjacent the inner surface 36 are desirably compatible with thermal bonding to the moisture barrier material. To the extent the fibrous compositions of the layers adjacent the moisture barrier 22 are chosen to be compatible with thermal bonding to the moisture barrier, the bond strength within the shaped structure 52 will be enhanced. Materials that are compatible in thermal bonding are those having similar softening temperatures, for instance within about 140 degrees Celsius, and which bond to one another when heated to the higher softening temperature.

The shape of the absorbent article 20 is designed to closely track that of the adult male anatomy, and thereby contribute to both performance and comfort. The shape may be characterized in terms of a Body Conforming Angle, a Skew Angle, a Resulting Length, and a Resulting Width of the shaped structure. The shaped structure 52 of FIG. 3 is shown positioned against horizontal and vertical surfaces 90 and 91 in FIG. 9A. The shape characteristics of the shaped structure 52 may be determined by collecting 10 representative structures. For each shaped structure 52, any adhesive release tape should be removed and the underlying adhesive blocked using glycerin, powder, and/or other suitable means. In the illustrated embodiment, the shaped structure 52 includes the moisture barrier 22, absorbent assembly 24 and liner 26. Each shaped structure 52 is conditioned by leaving it in a room which is 21±1 degree Celsius and 50±2 percent relative humidity for a period of two hours.

Figure 9A:
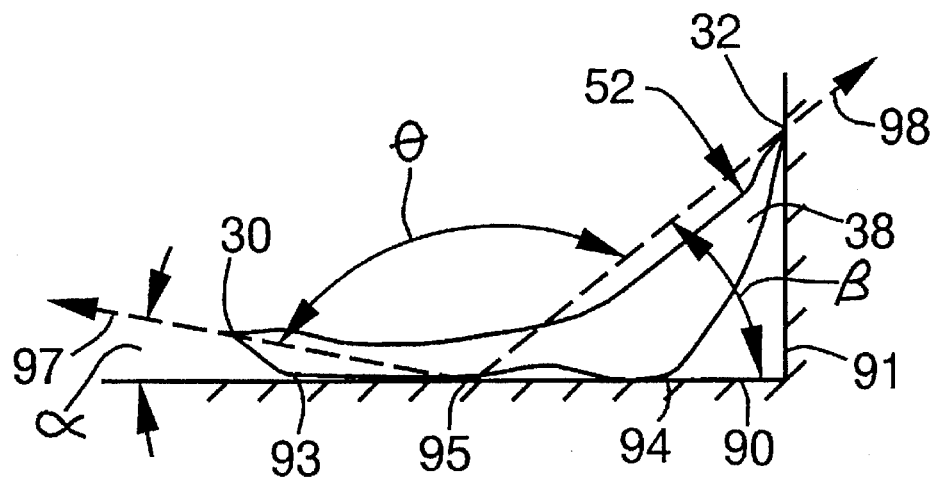

The outer surface 38 of each shaped structure 52 is placed against the horizontal surface 90 with the longitudinal axis of the structure perpendicular to the plane of the vertical surface 91. This may be accomplished by grasping the forward and rearward edges 30 and 32 of the shaped structure 52, positioning the edges approximately an equal distance from the horizontal surface 90, and lowering the shaped structure until the outer surface 38 just touches the horizontal surface. The edges 30 and 32 can then be released and the shaped structure allowed to drop to a normal rest position (FIG. 9A). The shaped structure 52 is then moved along the horizontal surface 90 until the structure just touches the vertical surface 91, the movement and contact being conducted so as to minimize compression of the structure. In particular, the rearward edge 32 is positioned toward the vertical surface 91, although the edge itself may not be the rearward portion of the shaped structure that just touches the vertical surface.

The location of the forwardmost point 93 of the outer surface 38 that is in contact with the horizontal surface 90 is noted. Similarly, the location of the rearwardmost point 94 of the outer surface 38 that is in contact with the horizontal surface 90 is noted. The distance between the forwardmost and rearwardmost points 93 and 94 is determined and the midpoint 95 therebetween is noted. Next, a ray 97 is identified extending from the midpoint 95 to the center of the forward edge 30. Also, a ray 98 is identified extending from the midpoint 95 to the center of the rearward edge 32, which may also be the point of contact with the vertical surface 91. Angle alpha ($\alpha$) between the horizontal surface 90 and ray 97, and angle beta ($\beta$) between the horizontal surface and ray 98, are determined for each article. The averages of alpha and beta angles for the 10 articles is calculated, and used to determine the Body Conforming Angle and Skew Angle for the article 20.

The Body Conforming Angle, illustrated as angle theta ($\theta$) in FIG. 9A, measures the longitudinal curvature of the shaped structure 52. The Body Conforming Angle is the angle between rays 97 and 98, and is equal to 180 degrees less the sum of angle alpha and angle beta. The Body Conforming Angle is desirably less than about 130 degrees, more desirably less than about 120 degrees, particularly about 115 degrees.

The Skew Angle measures the extent to which the rearward portion of the shaped structure 52 is curved in comparison to the forward portion. The Skew Angle is equal to angle beta minus angle alpha. The Skew Angle is desirably at least about 15 degrees, more desirably at least about 20 degrees, particularly about 40 degrees. The combination of the Body Conforming Angle and the Skew Angle as disclosed define shaped structures 52 that are tailored to the male anatomy by fitting closely against the genital region of the wearer.

So that the rearward edge 32 is positioned adjacent the perineum when in use, the Resulting Length of the shaped structure 52 is desirably from about 10 to about 25 centimeters, more desirably from about 13 to about 21 centimeters, particularly about 20 centimeters. The Resulting Length is equal to the distance between the center of the forward edge 30 to the vertical surface 91, measured parallel to the horizontal surface 90 and based on the average measurement for 10 articles 20.

Further, so that the shaped structure fits comfortably in the genital region of the wearer, the Resulting Width of the shaped structure 52 desirably narrows toward the rearward edge 32. The Resulting Width is the distance measured perpendicular to the longitudinal axis between longitudinally corresponding points on the side edges 34 of the shaped structure 52, based on the average measurement for 10 articles 20. As suggested particularly by FIG. 1, the Resulting Width may vary along the length of the article and narrows toward the rearward edge 32, and more desirably continually narrows from the forward edge 30 to the rearward edge. The Resulting Width desirably varies from about 7 to about 20 centimeters, particularly about 15 to 20 centimeters, adjacent the forward edge 30 and from about 2.5 to about 20 centimeters, particularly about 2.5 to about 7 centimeters, adjacent the rearward edge 32.

Figure 9B:
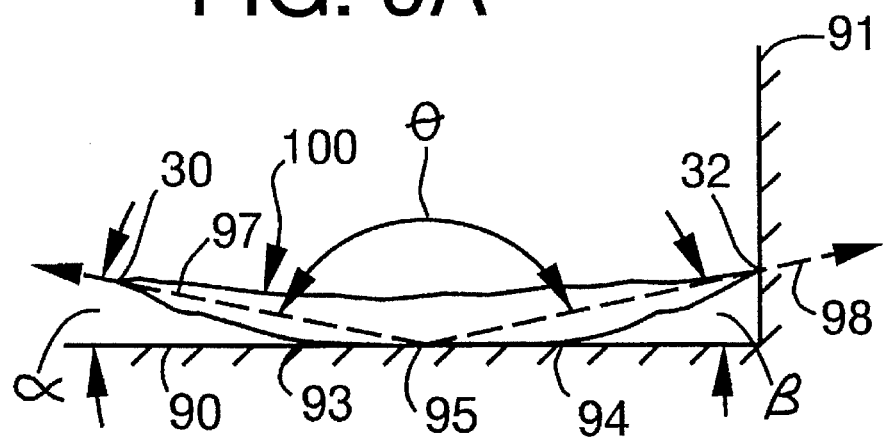
FIGS. 9B and 9C illustrate for purposes of comparison the shape of two absorbent products designed for females.
Figure 9C:
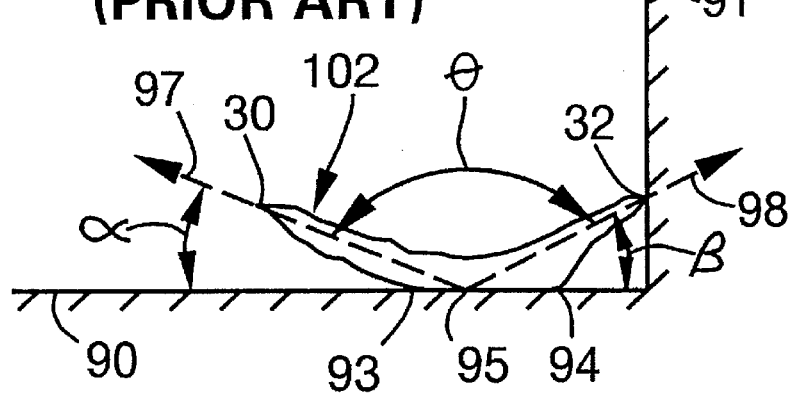

For purposes of comparison, two absorbent products designed for females are shown schematically in FIGS. 9B and 9C (not to scale). Absorbent article 100 of FIG. 9B represents an incontinence guard of the type previously sold by Kimberly-Clark Corporation under the tradename "DEPEND" "POISE" Feminine Guard. Ten articles 100 were examined and found to have a Body Conforming Angle of about 121 degrees and a Skew Angle of about 6 degrees. Similarly, absorbent article 102 of FIG. 9C represents a menstrual pad of the type sold by Kimberly-Clark Corporation under the tradename "KOTEX" Curved. Ten articles 102 were examined and found to have a Body Conforming Angle of about 124 degrees and a Skew Angle of about 8 degrees.

Figure 10:
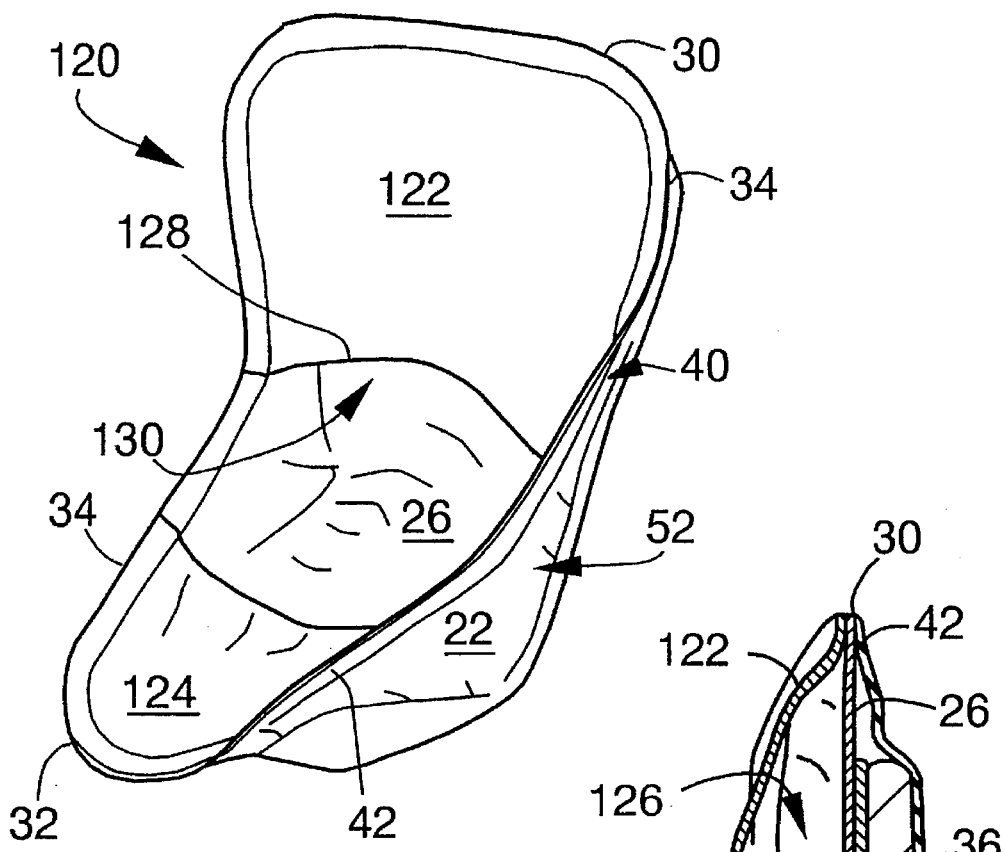
FIG. 10 is a perspective view of an alternate disposable absorbent article according to the present invention.
Figure 11:
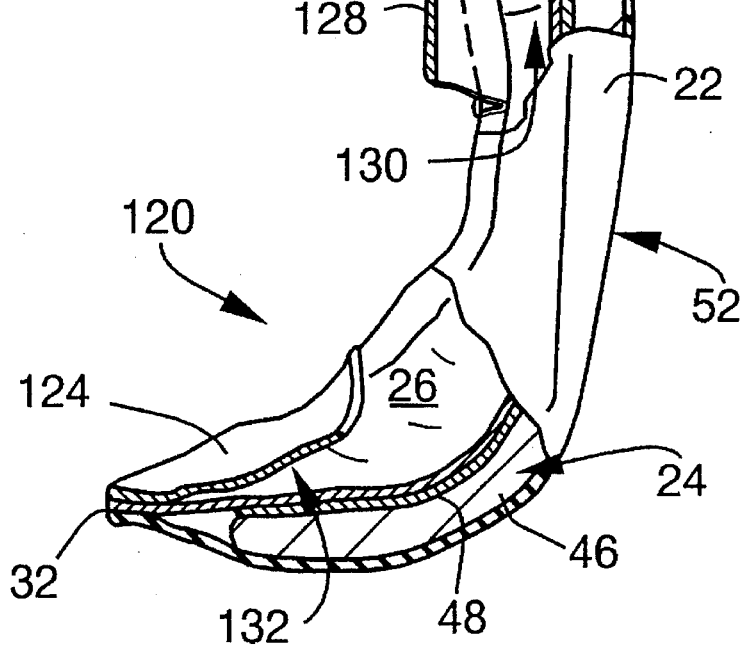
FIG. 11 is a side view of the absorbent article shown in FIG. 10, with portions broken away and shown in section for the purposes of illustration.

A further alternate embodiment of the present invention is illustrated by disposable absorbent article 120 in FIGS. 10 and 11. The absorbent article 120 represents a modification of the shaped structure 52 of FIG. 3, including the addition of a retaining member 122 and a cover 124. These components 122 and 124 are desirably added while maintaining the Body Conforming Angle, Skew Angle, Resulting Length, and Resulting Width as described above.

The retaining member 122 is attached to the moisture barrier 22 such that it defines a compartment 126 (FIG. 11) for retaining the penis of the wearer in the proper position near the absorbent assembly 24 during use of the absorbent article 120. The retaining member 122 may be bonded indirectly to the moisture barrier 22 and directly to the liner 26. The retaining member 122 desirably comprises a material that is vapor permeable and liquid impermeable. Suitable materials include films, nonwovens, laminates of films and nonwovens, or the like. For example, the retaining member 122 may be or comprise a cast or blown film formed of polypropylene, polyethylene., or the like, or a gas permeable thermal laminate comprising a polyethylene film and a polypropylene spunbond web.

A portion 128 of the periphery of the retaining member 122 is unattached to the moisture barrier 22 and/or liner 26. The unattached portion 128 is that portion of the periphery which extends between the opposite side edges 34 of the moisture barrier 22. The unattached portion 128 defines an opening 130 or point of entry to the compartment 126. To form the compartment 126, the retaining member 122 inward of its periphery is generally unattached to the liner 26. The remaining portions of the periphery of the retaining member 122 are desirably bonded to the rim 42 using thermal bonds, adhesives, ultrasonic bonds or other suitable means.

Alternately, the retaining member 122 could comprise one or more strips of material extending across the basin 40 (not shown). Such strips would also function to maintain the penis in proper position.

To fit a range of males, the unattached edge portion 128 and thus the opening 130 are desirably located within about 20 centimeters, more desirably within about 16 centimeters, from the rearward edge 32 of the moisture barrier 22. Further, the retaining member 122 and thus the compartment 126 extend from the opening 130 toward the forward edge 30 at least about 5 centimeters, desirably at least about 10 centimeters, and more desirably all the way to the forward edge. Accordingly, the retaining member 122 desirably has a surface area of from about 90 to about 210 square centimeters, particularly about 180 square centimeters.

The compartment 126 represents generally the volume beneath the retaining member 122, such as between the retaining member and the liner 26, that is available for the penis. The compartment 126 may have a volume of at least about 25 cubic centimeters, such as from about 25 to about 245 cubic centimeters, particularly about 125 cubic centimeters. The volume of the compartment 126 may be determined by estimating based on physical measurement the average dimensions of the compartment, or by another suitable method.

The cover 124 is attached to the moisture barrier 22 at the rearward end of the absorbent article 120 to minimize or prevent leakage from the rearward end and to keep the scrotum of the wearer dry. The cover 124 may be bonded indirectly to the moisture barrier 22 and directly to the liner 26 (see FIG. 11). The absorbent assembly 24 is positioned between the cover 124 and the moisture barrier 22. Desirably, the cover 124 is appropriately sized and bonded to the rim 42 of the moisture barrier 22 so that the center portion of the cover is suspended above the liner 26, for example by at least about 7 millimeters, such as from about 7 to about 15 millimeters, particularly about 10 millimeters, above the liner (see FIGS. 11 and 12). The cover 124 also provides a dry surface for the scrotum which is positioned against the cover during use. The cover 124 may be formed of a material that is substantially liquid impermeable and vapor permeable. Suitable materials may be or comprise a nonwoven web or cast or blown film formed of polypropylene, polyethylene, or the like, or a gas permeable thermal laminate comprising a polyethylene film and a polypropylene spunbond web.

The cover 124 may be bonded at its periphery to the moisture barrier rim 42 using thermal bonds, adhesives, ultrasonic bonds or other suitable means. Desirably, the bonded area extends completely along the rearward edge 32 and along a portion of the opposite side edges 34 near the rearward edge. The cover 124 desirably is not bonded to the liner 26 inward of the rim 42, but rather is suspended from the rim above the liner to form a chamber 132 (FIG. 11) between the liner and the cover. The chamber 132 desirably has a volume of from about 80 to about 160 cubic centimeters, particularly about 100 cubic centimeters. The volume of the chamber 132 may be estimated by the same method described for determining the volume of the compartment 126.

The cover 124 desirably has a surface area of at least about 13 square centimeters, such as from about 13 to about 194 square centimeters, particularly about 70 square centimeters. Also, the cover 124 is desirably spaced from the retaining member 122 by at least about 2 centimeters, such as about 5 centimeters, and located nearer the rearward edge 32.

Suitable supply means 136 may be included in the manufacturing process described above and illustrated in FIG. 4 to add the retaining member 122 and cover 124 to the shaped structure 52. The supply means 136 may be located after the thermoforming station 81 and prior to the trimming station 84. The retaining member 122 and cover 124 may be positioned over the basin 40 of the shaped structure 52 and bonded thereto using adhesives, thermal bonds, ultrasonic bonds or other suitable means. Desirably, the transverse axis of the articles 120 is parallel to the processing line direction, and continuous sheets of retaining member and cover materials are bonded to the composite web.

Figure 12:
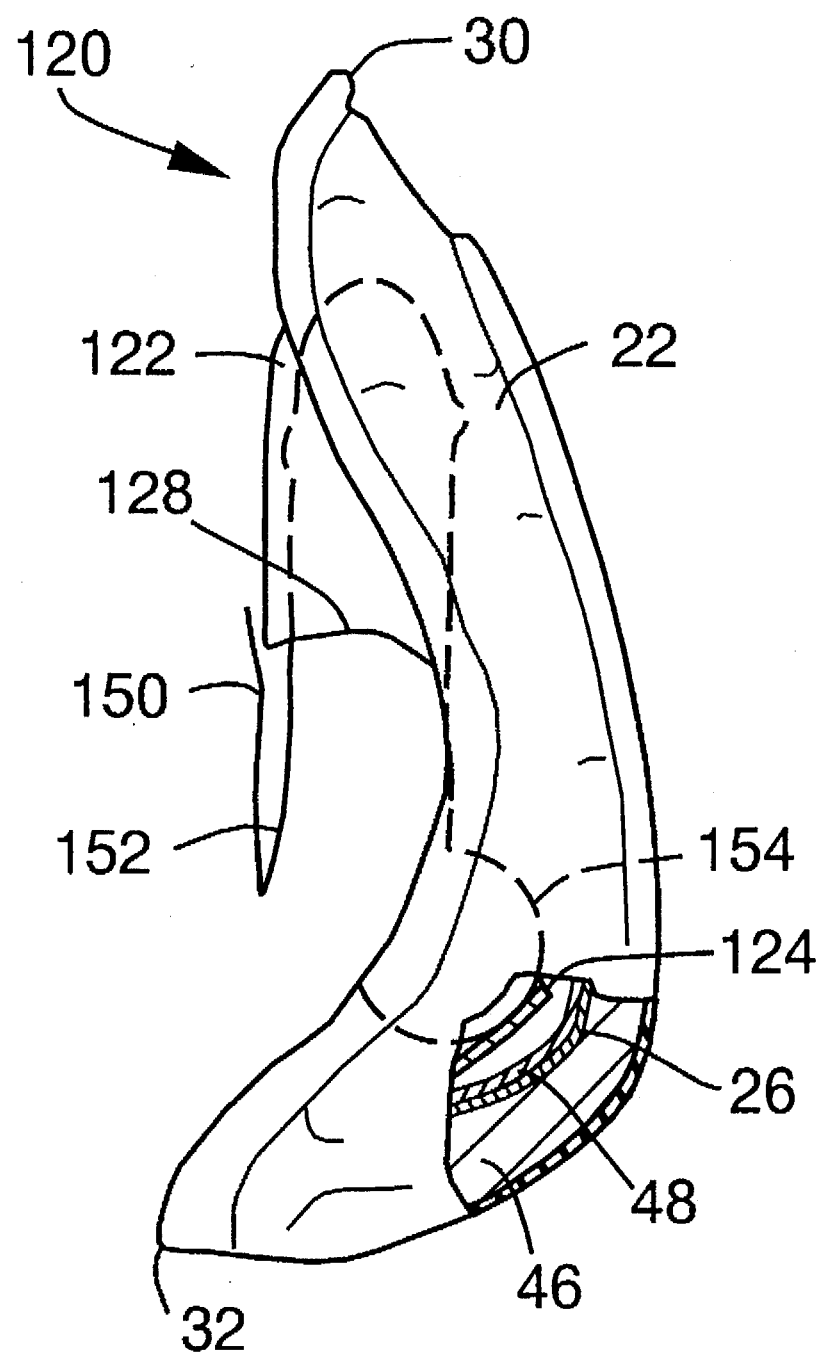
FIG. 12 is a side view of the absorbent article shown in FIG. 10, with portions broken away and shown in section for the purposes of illustration, and also including a representation of the male anatomy while the product is in use.
Figure 13:
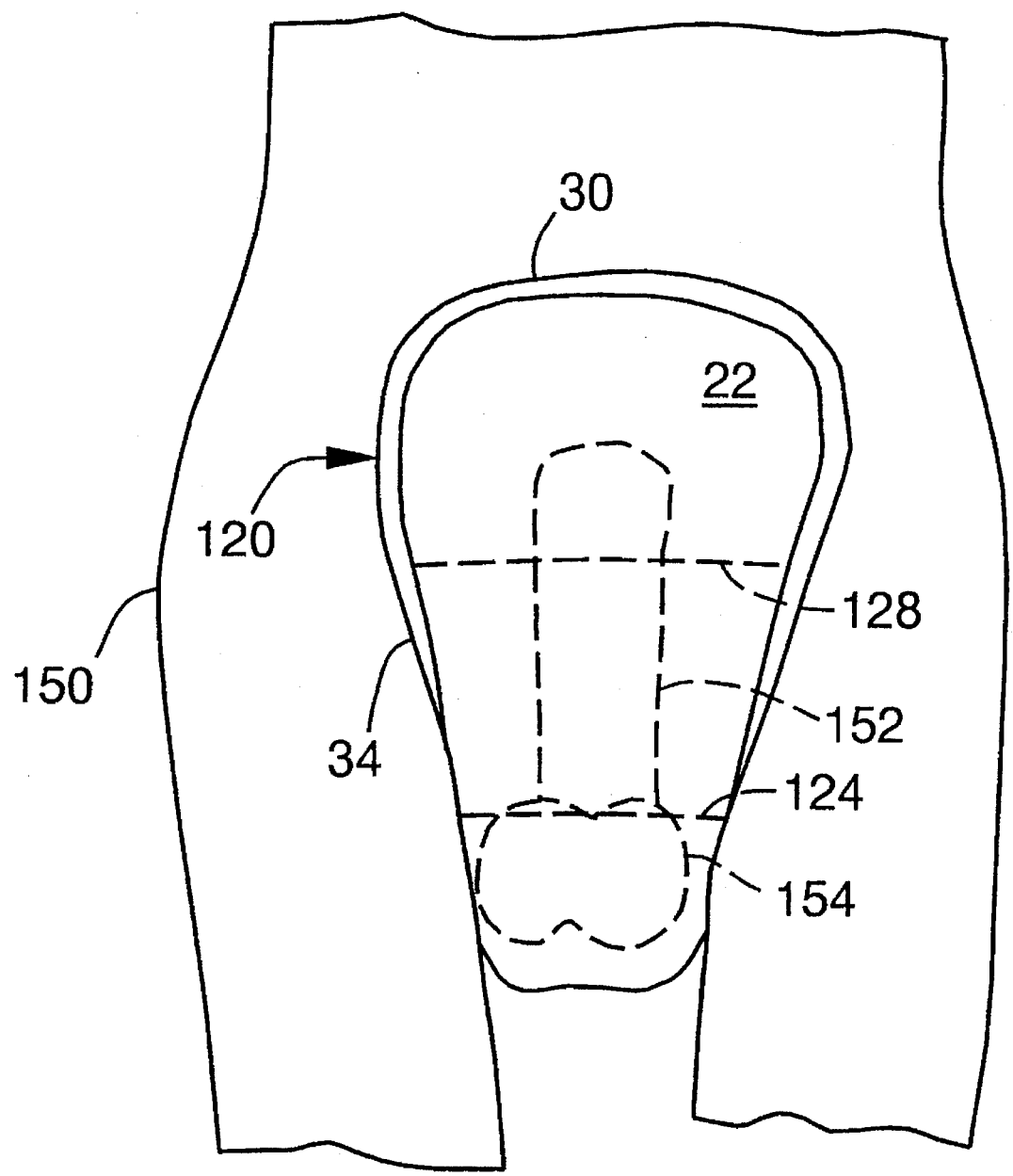
FIG. 13 is a front view of the disposable absorbent article shown in FIG. 10 including a representation of the male anatomy while the product is in use.

The absorbent article 120 is illustrated in use in the side view of FIG. 12 and the front view of FIG. 13. The article 120 is positioned on a male torso 150 such that the forward edge 30 is toward the front of the wearer and the rearward edge 32 is adjacent the perineum. The penis 152 of the wearer is inserted beneath the unattached portion 128 of the retaining member 122 to reside in the compartment 126, while the scrotum 154 of the wearer resides against the cover 124. The absorbent article 20 of FIG. 1 is used in a similar manner, although the penis and scrotum are both positioned against the liner and held in proper position by the peripheral wall 56.

Referring again to FIGS. 12 and 13, because the article 120 extends no further rearward than the perineum, the wearer generally does not sit on the article when seated. Additionally, the article 120 narrows toward the rearward edge 32 so that it can fit between the legs of the wearer. These aspects improve comfort over those incontinence products designed to collect both urine and feces. The absorbent assembly 24 is also subjected to fewer forces, such as those encountered during walking, which tend to bunch and twist the absorbent material. Further, because the peripheral wall 50 is ungathered due to the absence of elastic materials, there tends to be less skin irritation and discomfort, and more discretion due to a closer fit of the article 120.

The retaining member 122 assists in keeping the article 120 in a proper position in relation to the penis, both before and during urination without pressing tightly against the skin. The penis is maintained near the absorbent assembly 24, and urine is prevented from escaping by the moisture barrier 22, retaining member 122 and cover 124. In a particular embodiment, the cover 124 is suspended above the liner 26 and liquid moving toward the rearward edge 32, for example when the wearer is standing, will pass beneath the cover and be retained in the chamber 132. Further, the articles 20 and 120 provide sufficient air flow around the penis and scrotum by not surrounding them with absorbent material. In this regard, air flow in the articles 20 and 120 is enhanced because the height of the peripheral wall 56 above the absorbent assembly 24 transversely outward from the target zone 58 is greater than the height of the peripheral wall above the absorbent assembly longitudinally outward from the target zone. Also, the acquisition layer 48 and cover 124 (article 120) serve to keep the skin of the wearer dry after urination.

A wide variety of materials may be used to construct the aforementioned components of the absorbent articles 20 and 120. Numerous examples of materials used in constructing absorbent articles are described in the aforementioned U.S. patents incorporated by reference herein.

The liner 26 may be any soft, flexible, porous sheet which passes fluids therethrough. The liner 26 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The liner 26 has a pore size that readily allows the passage therethrough of liquids, such as urine and other body exudates. The liner 26 may be selectively embossed or perforated with discrete slits or holes extending therethrough, such as an apertured film material. Optionally, the web or sheet may be treated with a surfactant to aid in liquid transfer. One preferred liner material is a wettable spunbonded polypropylene having a basis weight of 24 grams per square meter. Such material may be produced by the methods and apparatus described in U.S. Pat. Nos. 4,340,563 and 4,405,297 to Appel et al., which are incorporated herein by reference.

The storage layer 46 is desirably an air-formed batt of cellulosic fibers (i.e., wood pulp fluff). One preferred type of wood pulp fluff, which is available under the trade designation CR1654 from Kimberly-Clark Corporation of Neenah, Wis., U.S.A., is a bleached, highly absorbent sulphate wood pulp containing softwood fibers. Optionally, the storage layer 46 could comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers.

The storage layer 46 may also include compounds to increase its absorbency, such as an effective amount of organic or inorganic high-absorbency materials. For example, the storage layer 46 can include 0-95 weight percent high-absorbency material. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine or the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Hoechst Celanese Corporation, and Allied Colloids, Inc. Typically, the high-absorbency material is capable of absorbing at least about 15 times its weight in water, and preferably is capable of absorbing more than about 25 times its weight in water.

The high-absorbency material can be distributed or otherwise incorporated into the storage layer 46 employing various techniques. For example, the high-absorbency material can be substantially uniformly distributed among the fibers comprising the storage layer. The materials can also be nonuniformly distributed within the storage layer fibers to form a generally continuous gradient with either an increasing or decreasing concentration of high-absorbency material, as determined by observing the concentration moving inward from the moisture barrier 24. Alternatively, the high-absorbency material can comprise a discrete layer separate from the fibrous material of the storage layer 46, or can comprise a discrete layer integral with the storage layer.

The storage layer 46 may also include a tissue wrap layer to help maintain the integrity of the fibrous core. This tissue wrap typically comprises a hydrophilic cellulosic material, such as creped wadding or a high wet-strength tissue.

In one embodiment, the storage layer 46 includes a mixture of wood pulp fluff and synthetic fiber having a basis weight of about 75 to about 500 grams per square meter, as well as an additional quantity, for instance about 50 grams per square meter or more, of high-absorbency material. The mixture may include from about 60 to about 90 percent wood pulp and from about 10 to about 40 percent of a synthetic fiber such as polypropylene, desirably about 70 percent wood pulp and about 30 percent synthetic fiber. The basis weight of the wood pulp fluff and synthetic fiber mixture desirably ranges from about 125 to about 175 grams per square meter for articles directed to lesser incontinence, and from about 175 to about 215 grams per square meter for articles directed to substantial incontinence.

Included among suitable components for acquisition layer 48 are substantially hydrophobic transport materials such as nonwoven polypropylene, polyethylene, polyester, blends thereof, or the like. The acquisition layer 48 may contain or be treated with a suitable surfactant to increase its initial wettability in adjustment of the performance of this invention. When treated with a surfactant, however, the acquisition layer 48 should still be less hydrophilic than the storage layer 46. The presence of an effective amount of surfactant on the acquisition layer 48 can advantageously increase the rate of movement of liquid into the storage layer 46 during initial insult of urine. After the initial insult, however, bodily discharges such as urine will continue to move through the acquisition layer 48 whether or not the surfactant is present therein. Accordingly, the surfactant may be water dispersible, if desired. Various surfactants are available, with one suitable surfactant being identified as Triton X-102 and available from Rohm and Haas Corporation of Philadelphia, Pa., USA.

The acquisition layer 48 may have a substantially uniform density throughout and an essentially or generally nonlayered configuration. The density, for instance, can be from about 0.015 to about 0.5 grams per cubic centimeter, and the thickness can be from about 0.3 to about 1.3 centimeters, such as about 0.6 centimeters. The acquisition layer may have a fiber denier from about 1.5 to about 15, and particularly from about 1.5 to about 6. The acquisition layer 48 may also have a pore size gradient therein, for instance, as having a series of stratified zones, or may have a substantially uniform porosity.

EXAMPLE

Ten shaped structures 52 of the type illustrated in FIG. 3 were constructed and their shape characteristics determined. The moisture barrier 22 was a cross-linked polyethylene foam containing a vinyl acetate comonomer, available from Voltek Inc. of Lawrence, Mass., USA, under the trade designation Volara. The foam material had a density of 64 kg/m$^3$ and a thickness of 1.5 millimeters. The liner 26 was a polyethylene spunbonded material having a basis weight of 20.4 grams per square meter. The storage layer 46 was a substantially uniform air-laid mixture of wood pulp fluff at 590 grams per square meter and a high-absorbency material at 275 grams per square meter. The acquisition layer was a latex-bonded carded web of polyester fibers material having a basis weight of 120 grams per square meter, available from Sackner Products of Grand Rapids, Mich. under the trade designation SN-92.

The moisture barrier and liner materials were each cut to form ten pieces measuring 45 by 45 centimeters. The storage layer 46 and acquisition layer 48 were cut to form ten irregularly shaped absorbent assemblies having a maximum length of 24 centimeters and a maximum width of 10 centimeters.

Ten composite structures each including a moisture barrier piece, a storage layer, an acquisition layer and a liner piece, in order, were assembled. Each composite structure was positioned in an oven maintained at 204.4 degrees Celsius for 7.6 seconds. This resulted in the moisture barrier and liner materials reaching a temperature of about 118.3 degrees Celsius. Each composite structure was then removed from the oven and immediately drawn by vacuum onto a mold surface of the type indicated in FIG. 6. The thus shaped structures were allowed to cool to room temperature for 20 to 30 minutes and hand trimmed.

The ten resulting shaped structures were measured and found to have a Body Conforming Angle of 115 degrees and a Skew Angle of 40 degrees. The Resulting Length was 20 centimeters and Resulting Width varied from 12.7 centimeters near the forward edge 30 to 2.5 centimeters near the rearward edge 32.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. For example, the retaining member 122 or cover 124 could be formed by a portion of the moisture barrier 22 folded over the absorbent assembly 24, or the cover 124 could be formed by a portion of the liner 26 being treated to be substantially liquid impermeable. Also, while the invention has been described with respect to use for male incontinence, certain of its advantages and features are adaptable for use in articles intended for female hygienic uses. Therefore, the invention should not be limited by the specific embodiments described, but only by the claims.

We claim:

1. An absorbent article having a longitudinal axis and a transverse axis, the absorbent article comprising:
    a shaped structure having opposite forward and rearward longitudinally-spaced edges and comprising a central portion with an ungathered peripheral wall outward of the central portion, the central portion comprising a target zone longitudinally separated from a secondary zone by a transition zone, the target zone located toward the forward edge and the secondary zone located toward the rearward edge, the peripheral wall transversely outward from the target zone having a height above the target zone of at least about 5 millimeters, the peripheral wall transversely outward from the transition zone having a height above the transition zone of at least about 25 millimeters, the shaped structure having a Resulting Length of from about 10 to about 25 centimeters, a Body Conforming Angle of less than about 130 degrees, and a Skew Angle of at least about 15 degrees, the shaped structure further comprising:
    a liquid storage layer having a periphery, the liquid storage layer located in the central portion and the peripheral wall located outward of the storage layer periphery;
    a moisture barrier formed of a formable, liquid impermeable material, the moisture barrier defining a basin having a length, width and volume with the liquid storage layer positioned in the basin; and
    a liner formed of a liquid permeable material bonded to the moisture barrier and sandwiching the liquid storage layer therebetween.

2. The absorbent article of claim 1 wherein the shaped structure has a Body Conforming Angle of less than about 120 degrees and a Skew Angle of at least about 20 degrees.

3. The absorbent article of claim 1 wherein the shaped structure has a Resulting Width that narrows toward the rearward edge.

4. The absorbent article of claim 1 wherein the peripheral wall transversely outward from the target zone has a height which is greater than the height of the peripheral wall longitudinally outward from the target zone.

5. The absorbent article of claim 1 wherein the absorbent article has a longitudinal center and the transition zone is located in a relatively curved and deep portion of the shaped structure between the longitudinal center and the rearward edge.

6. The absorbent article of claim 1 wherein the shaped structure further comprises a retaining member bonded to the moisture barrier, the retaining member defining a compartment between the liner and the retaining member, the compartment having a volume of at least about 25 cubic centimeters.

7. The absorbent article of claim 6 wherein the compartment has an opening located within about 20 centimeters of the rearward edge.

8. The absorbent article of claim 1 wherein the shaped structure further comprises a cover formed of a liquid impermeable material and bonded to the moisture barrier near the rearward edge, the cover having a surface area of from about 13 to about 194 square centimeters.

9. The absorbent article of claim 8 wherein a portion of the cover is suspended above the liner by at least about 7 millimeters.

10. An absorbent article having a longitudinal axis and a transverse axis, the absorbent article comprising:
    a liquid impermeable moisture barrier comprising a formable polymeric resin, the moisture barrier defining a forward edge, a rearward edge longitudinally spaced from the forward edge, a basin having a length, width and volume, and a rim about the basin, the moisture barrier having a length of from about 12 to about 38 centimeters and a width of from about 7 to about 20 centimeters;
    an absorbent assembly positioned in the basin and filling less than about 60 percent of the volume of the basin, the absorbent assembly comprising a liquid storage layer having a periphery; and
    a liquid permeable liner thermally bonded to the moisture barrier outward of the periphery of the storage layer, the absorbent assembly sandwiched between the moisture barrier and the liner;
    wherein the moisture barrier, absorbent assembly and liner define a shaped structure comprising a central portion with an ungathered peripheral wall outward of the central portion, the peripheral wall located outward of the periphery of the storage layer, the central portion comprising a target zone longitudinally separated from a secondary zone by a transition zone, the target zone located toward the forward edge and the secondary zone located toward the rearward edge, the peripheral wall transversely outward from the target zone having a height above the target zone of at least about 5 millimeters, the peripheral wall transversely outward from the transition zone having a height above the transition zone of at least about 25 millimeters, the shaped structure having a Resulting Length of from about 10 to about 25 centimeters, a Body Conforming Angle of less than about 130 degrees, and a Skew Angle of at least about 15 degrees.

11. The absorbent article of claim 10, further comprising a retaining member bonded to the rim and defining a compartment between the liner and the retaining member, the compartment having an opening and a volume of from about 25 to about 25 cubic centimeters, the opening located within about 20 centimeters of the rearward edge of the moisture barrier, the compartment extending from the opening toward the forward edge at least about 5 centimeters.

12. The absorbent article of claim 11, further comprising a cover formed of a liquid impermeable material and bonded to the rim, the cover having a surface area of from about 13 to about 194 square centimeters and being positioned between the opening and the rearward edge, the absorbent assembly sandwiched between the moisture barrier and the cover.

13. The absorbent article of claim 12 wherein a portion of the cover is suspended above the liner by at least about 7 millimeters.

14. The absorbent article of claim 10, further comprising:
   a retaining member bonded to the moisture barrier and defining a compartment between the liner and the retaining member, the compartment having an opening and a volume of at least about 25 cubic centimeters, the opening located within about 20 centimeters of the rearward edge of the moisture barrier, the compartment extending from the opening toward the forward edge at least about 5 centimeters; and
   a cover formed of a liquid impermeable material and bonded to the moisture barrier, the cover having a surface area of at least about 13 square centimeters and being positioned between the opening and the rearward edge, a portion of the cover being suspended above the liner by at least about 7 millimeters.

15. The absorbent article of claim 10 wherein the liner has a softening point that is within about 140 degrees Celsius of a softening point of the moisture barrier.

16. The absorbent article of claim 10 wherein the absorbent assembly further comprises an acquisition layer superposed on and in liquid communication with the storage layer, the storage layer having a urine capacity of from about 50 to about 300 grams.

17. The absorbent article of claim 10 wherein the shaped structure has a Body Conforming Angle of less than about 120 degrees and a Skew Angle of at least about 20 degrees.

18. The absorbent article of claim 10 wherein the shaped structure has a Resulting Width that narrows toward the rearward edge.

19. The absorbent article of claim 10 wherein the peripheral wall transversely outward from the target zone has a height which is greater than the height of the peripheral wall longitudinally outward from the target zone.

20. The absorbent article of claim 10 wherein the absorbent article has a longitudinal center and the transition zone is located in a relatively curved and deep portion of the shaped structure between the longitudinal center and the rearward edge.

* * * * *